(12) United States Patent
Snaidr (10) Patent No.: US 6,844,157 B2
(45) Date of Patent: Jan. 18, 2005

(54) METHOD OF DETECTING MICROORGANISMS IN A SAMPLE

(75) Inventor: Jiri Snaidr, Munich (DE)

(73) Assignee: Vermicon AG, Munich (DE)

(*) Notice: Subject to any disclaimer, the term of this patent is extended or adjusted under 35 U.S.C. 154(b) by 0 days.

(21) Appl. No.: 10/008,523

(22) Filed: Nov. 7, 2001

(65) Prior Publication Data

US 2003/0032007 A1 Feb. 13, 2003

Related U.S. Application Data

(63) Continuation of application No. PCT/EP00/03989, filed on May 4, 2000.

(30) Foreign Application Priority Data

May 7, 1999 (DE) .......................................... 199 21 281
Aug. 5, 1999 (DE) .......................................... 199 36 875

(51) Int. Cl.⁷ .......................... C12Q 1/68; C12P 19/34; C07H 21/02; C07H 21/04
(52) U.S. Cl. ........................ 435/6; 435/91.1; 435/91.2; 536/23.1; 536/23.5; 536/24.1
(58) Field of Search .............................. 435/5, 6, 91.1, 435/91.2; 536/23.1, 23.5, 24.1, 24.3, 23.7, 24.32, 24.33, 24.31

(56) References Cited

U.S. PATENT DOCUMENTS

| 5,750,340 | A | | 5/1998 | Kim et al. ....................... 435/6 |
| 5,888,725 | A | * | 3/1999 | Sanders ........................... 435/5 |
| 5,888,734 | A | | 3/1999 | Cremer et al. ................... 435/6 |
| 6,022,689 | A | | 2/2000 | Sarto et al. ...................... 435/6 |
| 6,090,627 | A | * | 7/2000 | Kemp et al. ................. 435/419 |

FOREIGN PATENT DOCUMENTS

| DE | 42 16 949 A1 | | 12/1993 | .......... G01N/33/68 |
| EP | WO 99/18234 | * | 4/1999 | ............ C12Q/1/68 |
| WO | 98/15656 | | 4/1998 | ............ C12Q/1/68 |
| WO | 99/18234 | | 4/1999 | ............ C12Q/1/68 |

OTHER PUBLICATIONS

Roe et al. "DNA ISolation and Sequencing" 1996 Appendix, solutions.*
Amann, R.I., et al., "Phylogenetic identification and in situ detection of individual microbial cells without cultivation", *Microbiological Reviews*, vol. 59, No. 1, pp. 143–169, (Mar. 1995) XP–002026194.
Mobarry, B.K., et al., "Phylogenetic probes for analyzing abundance and spatial organizaton of nitrifying bacteria", *Applied and Environmental Microbiology*, vol. 62, pp. 2156–2162, (Jun. 1996) XP–002068770.
Nordentoft, S., et al., "Evaluation of a fluorescence–labelled oligonucleotide probe targeting 23S rRNA for in situ detection of *Salmonella serovars* in paraffin–embedded tissue sections and their rapid identification in bacterial smears", *Journal of Clinical Microbiology*, vol. 35, No. 1, pp. 2642–2648, (Oct. 1997) XP–00262308.
Sambrook, et al., "Hybridization of radiolabaeled probes to immobilized nucleic acids", *Molecular Cloning—A Laboratory Manual*, Cold Spring Harbour Press (US), pp. 9.47–9.55, (1987) XP–002162309.

* cited by examiner

*Primary Examiner*—Jeffrey Fredman
*Assistant Examiner*—Sally Sakelaris
(74) *Attorney, Agent, or Firm*—Schwegman, Lundberg, Woessner & Kluth, P.A.

(57) ABSTRACT

The invention relates to a method for detecting microorganisms in a sample by means of a nucleic acid probe. Conventional detection methods are, for example, the in-situ hybridization of microorganisms with fluorescence-labeled oligonucleotide probes (fluorescent in-situ hybridization). A disadvantage of said method is that an epifluorescence microscope is required for evaluating the results. According to the invention, the disadvantages of the in-situ hybridization method are overcome by hybridizing the microorganisms to be detected in a sample with a specific nucleic acid probe, removing non-hybridized nucleic acid probe molecules, separating and then detecting and optionally quantifying the hybridized nucleic acid probe molecules.

21 Claims, 2 Drawing Sheets

METHOD OF DETECTING MICROORGANISMS IN A SAMPLE

RELATED APPLICATIONS

This application is a continuation under 35 U.S.C. 111(a) of International Application No. PCT/EP00/03989 filed May 4, 2000 and published as WO 00/68421 on Nov. 16, 2000, which claims priority under 35 U.S.C. 119 from German Application No. 199 21 281.3 filed May 7, 1999, and German Application No. 199 36 875.9 filed Aug. 5, 1999, all of which applications are incorporated herein by reference.

For many decades, microorganisms could be identified only after prior culturing of the microorganisms and amplification accordingly. In the case of viruses, the microorganisms are cultured on the respective host organism; in the case of bacteria, fungi and single-cell algae, the cells are cultured in culture media. Media and conditions which should largely prevent selective detection of certain groups are selected for detecting the number of viable microorganisms in a certain specimen. For example, pure cultures of individual bacterial colonies are prepared and then identified on the basis of phenotypic features such as their morphology and metabolic pathways. However, identification of microorganisms after prior culturing is associated with two important disadvantages. First, studies on a wide variety of environmental specimens have shown that only 0.1% to 14% of all bacteria can be cultured at the present time. Secondly, it has been demonstrated that extreme population shifts can occur in culturing, i.e., certain groups of bacteria are preferred in the laboratory and others are discriminated against.

This means not only that a majority of the bacteria in environmental samples cannot be identified, but also that those bacteria which are identified usually represent a distorted image of the true population structures. This results in incorrect estimates of the population ratios with respect to identification and quantification of bacteria.

At the beginning of the '90s, a method of in situ hybridization with fluorescence-labeled oligonucleotide probes was developed and has been used successfully in many environmental samples (Amann et al. (1990), J. Bacteriol. 172:762). This method, which is known as "FISH" (fluorescence in situ hybridization) is based on the fact that the ribosomal RNA (rRNA) present in each cell includes both highly conserved sequences, i.e., those with a low specificity, and less conserved sequences, i.e., genus-specific and species-specific sequences. By the middle of the '80s, it had been demonstrated that the sequences of the 16S— and 23S-rRNA can be used for identification of microorganisms (Woese (1987), *Microbiol. Reviews* 51:221; De Long et al. (1989), *Science* 243:1360). In the case of the FISH method, fluorescence-labeled gene probes whose sequences are complementary to a certain region on the ribosomal target sequences are introduced into the cells. The probe molecules are usually 16- to 20-base-long, single-stranded deoxyribonucleic acid fragments, and they are complementary with a target range which is specific for a certain species or genus of bacteria. If the fluorescence-labeled gene probe finds its target sequence in a bacterial cell, it binds to it, and the cells can be detected on the basis of their fluorescence in a fluorescence microscope.

It has been demonstrated that up to 90% of a total bacterial population can be detected by in situ hybridization with fluorescence-labeled probes. Therefore, this method represents a significant improvement in comparison with the state of the art, which has made it possible to detect a maximum of 14% of the bacterial population in an environmental specimen. In addition, the method of in situ hybridization with fluorescence-labeled probes makes it possible to determine the active portion of a population by determining the ratios of a probe directed against all bacteria relative to the dry weight. Finally, this method makes it possible to visualize bacteria directly at their site of action, which thus makes it possible to detect and analyze interactions between different bacterial populations.

Within recent years, the technique of in situ hybridization with fluorescence-labeled probes has been tested and used successfully with a wide variety of environmental samples. Thus, by using gene probes in soil, protozoa, biofilms, air, lake water, biologically activated filters and wastewater from sewage treatment facilities, it has been possible to investigate the respective bacterial populations and identify new types of bacteria. The main point of emphasis here has been analysis of the bacterial populations in wastewater purification. Trickle filters, room filters and activated sludge installations have been investigated, along with secondary clarification ponds and corresponding receiving streams (Snaidr et al. (1997), *Appl. Environ. Microbiol.* 63:2884). It has been shown by means of the in situ hybridization technique that when activated sludge flora are detected by culturing, there is a culturing shift (Wagner et al. (1993), *Appl. Environ. Microbiol.* 59:1520). Therefore, methods that depend on culturing give a highly distorted view of the composition and dynamics of the microbial biocenosis. The significance of bacteria, which play only a subordinate role in activated sludge but are well adapted to the given culturing conditions, is dramatically overestimated due to this distortion of the actual conditions within the bacterial population which occurs as a function of the medium. It has thus been demonstrated that because of such a culturing artefact, the role of the bacterial genus *Acinetobacter* as a biological agent for removing phosphates in wastewater purification has been completely misappraised.

Although in situ hybridization with the newly developed fluorescence-labeled gene probes permits a rapid and accurate analysis of bacteria populations in wastewater, it has not yet been successful in practice. Reasons for this include the high cost of acquisition of the necessary technical equipment such as a fluorescence microscope, the demand for qualified personnel, who must be available to perform the tests and analyze the results, as well as the resulting low number of possible reference measurements. In addition, it is very time-consuming to count the bacterial populations thus detected (quantification). Moreover, such counts require high empirical values because it is necessary to differentiate between true signals (probe binding has in fact occurred) and false signals (autofluorescence, no cells).

Therefore, the object of the present invention is to make available a method with which microorganisms can be detected and optionally quantified, preferably without prior culturing.

Another important object of the present is to provide a method of detecting microorganisms, to be carried out under conditions which guarantee that the measurement results will not be influenced in a negative sense by detection and quantification, if desired.

Furthermore, another object of the present invention is to provide a method for detection of microorganisms which can be carried out more rapidly and in a more environmentally friendly manner and is easier to handle than the methods described in the state of the art.

According to this invention, these objects are achieved by a method for detecting microorganisms in a sample by means of a nucleic acid probe, where this method includes the following steps:
a) fixation of the microorganisms present in the sample;
b) incubation of the fixed microorganisms with detectable nucleic acid probe molecules to induce hybridization;
c) removing unhybridized nucleic acid probe molecules;
d) isolating the hybridized nucleic acid probe molecules, and
e) detecting and optionally quantifying the isolated nucleic acid probe molecules.

Within the context of the present invention, the term "fixation" of microorganisms should be understood to refer to a treatment with which the coat or shell surrounding the respective microorganism is made so permeable that the nucleic acid probe having the optionally covalently bonded labeling can penetrating through the coat to reach the target sequences in the interior of the cell. The coat may be a lipid coat surrounding a virus, for example, the cell a wall of a bacterium or the cell membrane of a single-cell microorganism. A paraformaldehyde solution with a low percentage concentration is generally used for the fixation. If, in the individual case, the protective coat surrounding a microorganism cannot be made penetrable with a paraformaldehyde solution, those skilled in the art will be familiar with sufficient other measures leading to the same result. Such measures would include for example, ethanol, methanol, mixtures of these alcohols with paraformaldehyde, enzymatic treatments, ultrasonic treatment, etc.

In the case of a nucleic acid probe in the sense of this invention, it may be a DNA or RNA probe, which usually comprises between 12 and 1000 nucleotides, preferably between 12 and 100 or 15 and 50 nucleotides, especially preferably between 17 and 25 nucleotides. The nucleic acid probe is selected so that there is a sequence complementary to it in the microorganism to be detected or in the group of microorganisms to be detected. In the case of a probe with only approximately 15 nucleotides, the requirement of complementarity must be met over 100% of the sequence; in the case of oligonucleotides with more than 15 nucleotides, one or more mismatched sites are allowed. However, it must be guaranteed that the nucleic acid probe molecule will in fact hybridize with the target sequence under moderate and/or stringent hybridization conditions. Moderate conditions in the sense of this invention would include, for example, 0% formamide in a hybridization buffer such as that described in Example 1. Stringent conditions in the sense of this invention would include, for example, 20% to 80% formamide in the buffer described in section 5.2 of Example 1.

The duration of hybridization is usually between 10 minutes and 12 hours. Hybridization preferably takes place for about two hours. The hybridization temperature is preferably between 44° C. and 48° C., especially preferably 46° C., where the parameter of the hybridization temperature as well as the concentration of salts and detergents in the hybridization solution can be optimized as a function of the probe or probes, in particular their length(s) and the degree of complementarity with the target sequence in the cell to be detected. Those skilled in the art will be familiar with the relevant calculations in this regard.

In the scope of the method according to this invention, a typical hybridization solution would have a salt concentration of 0.1 M to 1.5 M, preferably 0.9 M, with the salt preferably being sodium chloride. In addition, the hybridization buffer usually includes a detergent such as sodium dodecyl sulfate (SDS) in a concentration of 0.001 to 0.1%, preferably in a concentration of 0.01%, and Tris/HCl in a concentration range of 0.001–0.1 M, preferably in a concentration of 0.02 M. The pH value of Tris/HCl is usually between 6 and 10, but a pH of approximately 8.0 is preferred. As mentioned above, the hybridization solution may also contain between 0% and 80% formamide, depending on the degree of stringency desired or required.

If possible, the nucleic acid probe should be present in the hybridization buffer in an amount of 15 ng to 1000 ng, with this amount preferably being in 80 $\mu$L hybridization solution. The probe concentration especially preferably amounts to 125 ng/80 $\mu$L hybridization solution.

After successful hybridization, the unhybridized and excess probe molecules should be removed, which is usually accomplished by means of a traditional washing solution or washing buffer. The washing buffer usually contains 0.001% to 0.1% of a detergent such as SDS, with a concentration of 0.01% being preferred, and Tris/HCl in a concentration of 0.001 to 0.1 M, preferably 0.02 M, with the pH value of Tris/HCl being in the range of 6.0 to 10.0, preferably 8.0. In addition, the washing buffer usually contains NaCl, but the concentration amounts to between 0.003 M and 0.9 M, preferably between 0.01 M and 0.9 M, depending on the stringency required. In addition, the washing solution may also contain EDTA, in which case the concentration is preferably 0.005 M.

The unbound probe molecules are usually "washed out" at a temperature in the range of 44° C. to 52° C., preferably between 46° C. and 50° C., and especially preferably at 48° C. for a period of 10 to 40 minutes, preferably for 20 minutes.

After successful in situ hybridization, followed by removal of the unhybridized nucleic acid probe molecules by means of the washing step described above, the hybridized probe molecules are isolated for detection, and if desired, the hybridized probe molecules are quantified.

For this extraction step, extraction agents which guarantee denaturing of the probe from the target sequence at a suitable temperature without damaging the probe molecule to any significant extent are suitable for this extraction step. The latter is desirable in particular in order not to have a negative effect on the measurement results in the subsequent detection and quantification. The preferred separation solution or buffer for this purpose is water, i.e., distilled or double-distilled $H_2O$ or weakly buffered water, i.e., for example, Tris/HCl in a concentration range of 0.001 M to 1.0 M, especially preferably in a concentration of 0.01 M, with the pH of Tris/HCl being between 7.0 and 11.0, preferably 9.0. In addition, DMSO (dimethyl sulfoxide) and 1×SSC, pH 10.0 (+/−2.0) are also suitable extraction agents for use according to this invention, in which case 1×SSC is suitably prepared by diluting a 20×SSC stock solution (175.2 g NaCl, 88.2 g sodium citrate, adding water to a total of one liter).

Separation of the probe molecules is usually performed for a period of 5 to 30 minutes, preferably 15 minutes. Probe extraction is performed in a temperature range of 50 to 100° C., preferably 100° C., especially preferably at approximately 80° C. In any case, an attempt should be made to perform the extraction at a temperature which is effective but at the same time guarantees gentle separation of the probe molecules. Since the probes are less affected by the extraction treatment as the temperature is lower, a temperature of <100° C., especially <90° C. is preferred.

In a comparion experiment, 4.8×10$^6$ *Burkholderia cepacia* cells were hybridized with two fluorescence-labeled oligonucleotide probes (each 2.5 $\mu$L BET42a-Cy3 or NonEUB338-Cy3) by means of the fast FISH method according to this invention. Probe extraction was performed for 15 minutes at 80° C. with 110 $\mu$L separation solution, comparing double-distilled H$_2$O, 0.01 M Tris/HCl, pH 9.0, 1×SSC, pH 10.0, DMSO and formamide with one another with regard to the measurement signal, i.e., the fluorescence intensity. Although good to very good results were achieved with water, 0.01 M Tris/HCl, 1×SSC and DMSO, no comparable measurement signal comparable to probe extraction with the other separation solutions could be obtained when using formamide. Instead, the signal that was obtained with formamide as the extraction solution was lower by a factor of at least 10 than the intensities measured with double-distilled H$_2$O or 0.01 M Tris/HCl, for example. At a separation temperature of 100° C. (i.e., an extraction agent temperature of 100° C.), the difference in the measurement signals was even more pronounced between formamide on the one hand and double-distilled H$_2$O or 0.01 M Tris/HCl on the other hand. These observations can in all probability be attributed to an even greater negative effect of formaldehyde on the probe molecules at higher temperatures.

On the basis of these observations, double-distilled H$_2$O or 0.01 M Tris/HCl in particular is preferred as the extraction agent in comparison with formamide, which is usually recommended as the extraction agent in the state of the art. Due to the fact that formamide is not used in the extraction step, not only is the resulting treatment less damaging, but also there are additional advantages with regard to the potential hazard involved with formamide, which is a substance of toxicity class 3. In addition, the use of formamide is much more cost-intensive in comparison with water or weakly buffered water.

The respective nucleic acid probe is selected as a function of the microorganism to be detected. For example, if only microorganisms of the species Streptococcus salivarius are to be detected, but microorganisms of the species Streptococcus thermophilus are not to be detected, then those skilled in the art will select a suitable sequence which occurs in Streptococcus salivarius but does not occur in Streptococcus thermophilus. These sequences are typically selected from the 16S-rRNA or the 23S-rRNA. However, if all the bacteria of the genus Streptococcus are to be detected, then a sequence which is found in common in both Streptococcus salivarius and Streptococcus thermophilus as well as additional species of the genus Streptococcus would be selected. Many examples of such sequences have already been published in the literature (see, for example, Beimfohr et al. (1993), System Appl. Microbiol. 16:450). The nucleic acid probe may be complementary to a chromosomal or episomal DNA, but it may also be complementary to an mRNA or an rRNA of the microorganism to be detected. The preferred nucleic acid probes for selection are those which are complementary to a range occurring in the respective microorganism to be detected in more than one copy. The sequence to be detected preferably occurs 500 to 100,000 times per cell, especially preferably in 1000 to 50,000 times. This is another reason why it is especially preferable for the nucleic acid probe to be complementary to an rRNA: ribosomal RNA is part of ribosomes which are present many thousand times in each active cell because they are protein synthesis molecules.

According to this invention, the nucleic acid probe is incubated with the fixed microorganism in the above-mentioned sense, in order to thereby permit penetration of the nucleic acid probe molecules into the microorganism and hybridization of nucleic acid probe molecules with the nucleic acids of the microorganisms. Following that, non-hybridized nucleic acid probe molecules are removed by the usual washing steps. In contrast with the traditional FISH method, however, now the hybridized nucleic acid probe molecules are not left in situ, i.e., in the respective microorganism, but instead they are isolated again from the nucleic acid to be detected and are separated from cellular constituents, detected and optionally quantified. The prerequisite for this is that the nucleic acid probe molecule used according to this invention can be detected. This detectability can be ensured, for example, by covalent bonding of the nucleic acid probe molecule to a detectable marker. Detectable markers usually include fluorescent groups such as Cy-2, Cy-3 or Cy-5, FITC, CT, TRITC or Fluos-Prime, all of which will be very familiar to those skilled in the art. For the sake of thoroughness, Table 1 below lists a few markers, their properties and sources for ordering them.

TABLE 1

| | |
|---|---|
| FLUOS: | 5,(6)-carboxyfluorescein-N-hydroxysuccinimide ester (Boehringer Mannheim, Mannheim, Germany); $\epsilon = 7.50 \times 10^4$ mol$^{-1}$L$^{-1}$, abs$_{max}$ at 494 nm; Em$_{max}$ at 518 nm, mol. wt. = 473. |
| TRITC: | tetramethylrhodamine 5,6-isothiocyanate (Isomer G, Molecular Probes Inc., Eugene, USA, Lambda, Graz, Austria); $\epsilon = 1.07 \times 10^5$ mol$^{-1}$L$^{-1}$, abs$_{max}$ at 537 nm; Em$_{max}$ at 566 nm, mol. wt. = 479. |
| CT: | 5,(6)-carboxytetramethylrhodamine N-hydroxysuccinimide ester (Molecular Probes Inc., Eugene, USA); $\epsilon = 0.87 \times 10^5$ mol$^{-1}$L$^{-1}$, abs$_{max}$ at 537 nm; Em$_{max}$ at 566 nm. |
| CY-3: | NHS ester of Cy5.18 (Biological Detection Systems, Pittsburgh, USA); (Amersham Life Sciences, Inc., Arlington Heights, USA); $\epsilon = 1.5 \times 10^5$ mol$^{-1}$L$^{-1}$, abs$_{max}$ at 532 nm; Em$_{max}$ at 565 nm, mol. wt. = 765.95. |
| CY-5: | NHS ester of Cy5.18 (Biological Detection Systems, Pittsburgh, USA); (Amershal Life Sciences, Inc., Arlington Heights, USA); $\epsilon = > 2 \times 10^5$ mol$^{-1}$L$^{-1}$, abs$_{max}$ at 650 nm; Em$_{max}$ at 667 nm, mol. wt. = 791.99. |

When using fluorescent markers, the method according to invention is also referred to below as a "fast FISH" method, based on the terminology used for the above-mentioned FISH method.

As an alternative, chemoluminescent groups or radioactive markers such as $^{35}$S, $^{32}$P, $^{33}$P, $^{125}$I may be used. However, detectability may also be ensured by coupling the nucleic acid probe molecule with an enzymatically active molecule such as alkaline phosphatase, acid phosphatase, peroxidase, horseradish peroxidase, β-D-galactosidase or glucose oxidase. For each of these enzymes, there are a number of known chromogens which can be reacted instead of the natural substrate and can be converted either to colored or fluorescent products. Examples of such chromogens are given in Table 2 below.

TABLE 2

| Enzyme | Chromogen |
|---|---|
| 1. Alkaline phosphatase and acid phosphatase | 4-Methylumbelliferyl phosphate*, bis (4-methylumbelliferyl phosphate)*, 3-O-methylfluorescein, flavone 3-diphosphate triammonium salt*, p-nitrophenyl phosphate disodium salt |

TABLE 2-continued

| Enzyme | Chromogen |
| --- | --- |
| 2. Peroxidase | tyramine hydrochloride*, 3-(p-hydroxyphenyl) propionic acid*, p-hydroxyphenethyl alcohol*, 2,2'-azino-di-3-ethylbenzothiazoline sulfonic acid (ABTS), ortho-phenylenediamine dihydrochloride, o-dianisidine, 5-aminosalicylic acid, p-ucresol*, 3,3'-dimethyloxybenzidine, 3-methyl-2-benzothiazoline hydrazone, tetramethylbenzidine |
| 3. Horseradish peroxidase | $H_2O_2$ + diammoniumbenzidine, $H_2O_2$ + tetramethylbenzidine |
| 4. β-D-galactosidase | o-Nitrophenyl-β-D-galactopyranoside, 4-methylumbelliferyl-β-D-galactoside |
| 5. Glucose oxidase | ABTS, glucose and thiazolyl blue |

*Fluorescence

Finally, it is possible to design the nucleic acid probe molecules so that another nucleic acid sequence which is suitable for hybridization is present at its 5'- or 3'-end. This nucleic acid sequence in turn includes approximately 15 to 1000 nucleotides, preferably 15 to 50 nucleotides. The second nucleic acid range may in turn be recognized by oligonucleotide probes which can be detected by one of the means mentioned above.

Another possibility is coupling the detectable nucleic acid probe molecules with a haptene. After separation of the nucleic acid probe molecules from the target nucleic acid, the nucleic acid probe molecules which are then separate can be brought in contact with detectable antibodies that recognize the haptene. A known example of such a haptene is digoxigenin or its derivatives. Those skilled in the art will be familiar with many additional possibilities in addition to those given in the examples for detecting and quantifying an oligonucleotide that is used for hybridization.

The plurality of possible markings also permits simultaneous detection of two or more different overlapping or nonoverlapping populations. For example, by using two different fluorescence markers, it is possible to detect *Streptococcus salivarius* as well as *Streptococcus thermophilus* or *Streptococcus salivarius* in addition to the total streptococcal population.

The microorganism to be detected by the method according to this invention may be a prokaryotic or eukaryotic microorganism. In most cases, it is desirable to detect single-cell microorganisms. Relevant microorganisms include mainly yeasts, bacteria, algae and fungi.

In an especially preferred embodiment of the invention, the microorganism is a member of the genus *Salmonella*.

The method according to this invention may be used in a variety of ways. For example, it is suitable for investigating environmental samples for the presence of certain microorganisms. These environmental samples can be obtained from water, soil or air. Normally no prior culturing is necessary for detection of certain bacteria in environmental samples.

Another important application for the method according to this invention is for inspection of food samples. In preferred embodiments, the food samples are taken from milk or milk products (yogurt, cottage cheese, hard cheese, butter, buttermilk), drinking water, beverages (juice, lemonade, beer), bakery goods or meat products. Under some circumstances, prior culturing may be desirable or even required for detection of microorganisms in foods. For example, for detection of a single organism of *Salmonella* in 25 mL milk, the milk must first be cultured for a period of time to then find one or more *Salmonella* in the sample volume with a statistical reliability.

The method according to this invention can also be used for testing medical samples. It is suitable for testing tissue samples such as biopsy material taken from the lung, from a tumor or inflammatory tissue, from secretions such as perspiration, saliva, sperm and secretions from the nose, urethra or vagina or for urinalysis and stool specimens.

Another area of application of the method according to this invention is for testing wastewater such as activated sludge, putrefactive sludge or anaerobic sludge. In addition, it is suitable for analyzing biofilms in industrial installations as well as naturally occurring biofilms or biofilms formed in wastewater purification. Finally, it is also suitable for testing and for quality control of pharmaceutical and cosmetic products such as creams, ointments, tinctures, liquids, etc.

The method according to this invention represents a possibility of establishing in situ hybridization for cell identification and optionally quantification in practice. The required equipment would be limited to the acquisition of a fluorometer (max. approximately DM 18,000), for example, when using fluorescent molecular probes. In contrast with that, an epifluorescence microscope, which is suitable for carrying out the traditional FISH method and with which sufficiently good in situ hybridization results can be achieved, is in a price range of approximately 100,000 DM. Furthermore, when using Cy-5 labeled probes, for example, the epifluorescence microscope must also be equipped with a high-quality CCD camera (price between DM 30,000 and DM 50,000). For this reason, the method according to this invention is a much less expensive measurement method than the time-consuming quantification using an epifluorescence microscope. Moreover, the ongoing cost of the method according to this invention using a fluorometer is much lower than that of the traditional method using epifluorescence microscopy. This is due mainly to the fact that the mercury high pressure lamps (each DM 450) of the epifluorescence microscope must be replaced at the latest after 100 hours of operation for reasons of quality and safety. The enormously time-consuming process of counting specifically labeled cells under the microscope thus leads to great wear and tear on the lamp. The xenon arc lamp of a fluorometer (DM 3000) has a lifetime of one to three years even with extensive use of the instrument. The cost of the personnel required to perform the measurements represents an additional cost factor. Although a quantitative analysis of an environmental sample by means of the traditional method requires several days, especially when multiple probes are used, the method according to this invention should handle this job within a few hours. For hybridization and extraction, a period of three hours would be needed, whereas quantification in a fluorometer would take only a few minutes. Quantification could also be performed by untrained personnel, whereas with the traditional method, visual quantification requires the skills of a specialist.

Thus, the present invention makes available a method which can be carried out much more easily and more rapidly in comparison with the traditional methods and is also safer for the environment.

Although this invention has been described essentially with respect to fluorescence-labeled probe molecules, it is self-evident that the above-mentioned advantages are also obtained when using other markers.

According to this invention, a kit is made available for carrying out the method for detecting microorganisms in a sample. The contents of such a kit will depend essentially on the nature of the microorganism to be detected. It will include as the most important component a nucleic acid probe which is specific for the respective microorganisms to be detected as well as another nucleic acid probe with which a negative control can be performed. In addition, it includes a hybridization buffer and optionally a lysis buffer. The choice of the hybridization buffer will depend primarily on the length of the nucleic acid probes used. Thus, as those skilled in the art will be aware, less stringent conditions are necessary for hybridization of a nucleic acid probe which is 15 nucleotides long than for hybridization of a probe 75 nucleotides long. Examples of hybridization conditions are given, e.g., by Stahl & Amann (1971) in Stackebrandt and Goodfellow (eds.), *Nucleic Acid Techniques in Bacterial Systematics*; John Wiley & Sons Ltd., Chichester, UK.

The composition of the lysis buffer also depends on the respective microorganism. Thus, slightly different conditions are necessary for lysis of viral coats, cell walls of gram-positive or gram-negative bacteria, and cell membranes of yeasts or algae, but these conditions can be determined readily in the respective literature.

In a preferred embodiment, the kit according to this invention contains specific probes for detection of bacteria of the genus *Salmonella*. In an especially preferred embodiment, the nucleic acid probe molecule for specific detection of a microorganism is the nucleic acid sequence:

Salm 63: 5'-TCGACTGACTTCAGCTCC-3' (SEQ ID NO: 1)

and in the case of the negative control it is the sequence:

NonSalm: 5'-GCTAACTACTTCTGGAGC-3' (SEQ ID NO:2)

or a nucleic acid probe molecule which differ from Salm63 and/or NonSalm by a deletion and/or an addition, but the ability of these probes to hybridize with *Salmonella*-specific nucleic acid is maintained, or they may be nucleic acid probe molecules which can hybridize with the aforementioned nucleic acids.

The following illustrations and the examples are presented to illustrate this invention and should not be interpreted as restricting the scope in any way.

FIGURES

The mixture of cells, some of which have bound nucleic acid probe molecules of type A, is put through a separation step. Then the nucleic acid probe molecules of type A separated in this way are quantified.

Figure 1:
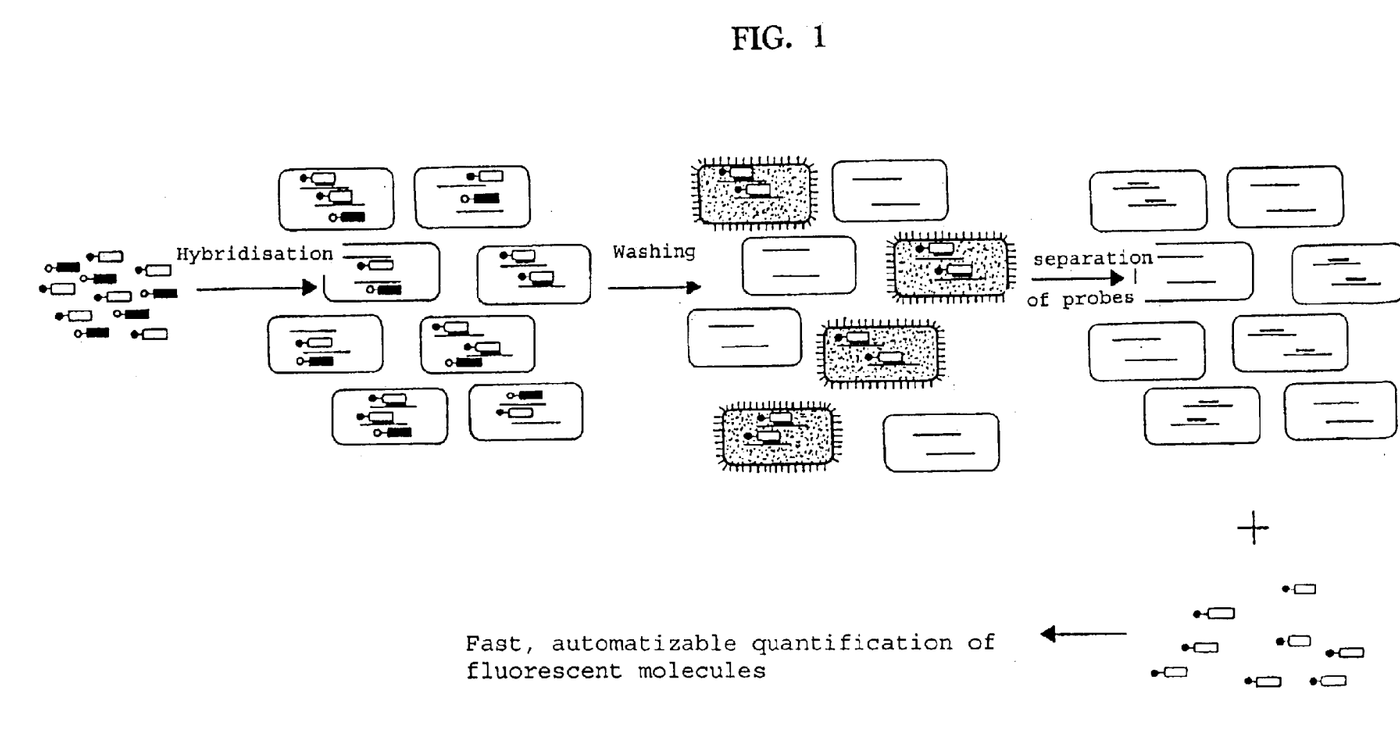
FIG. 1 illustrates how the method according to this invention for detection of cells of a type A can be used while at the same time excluding the presence of cells of type B. To do so, nucleic acid probes which are specific for cell types A and B are prepared and hybridized with the sample to be tested. During the hybridization process, the differently labeled probes A and B penetrate into cells of types A and C. Only the cell of type A contains the target nucleic acid having the binding sites for probes of type A but not cell C. In addition, neither of the two cells has binding sites for probes of type B, which is therefore not bound. After the subsequent washing step, the cells contain only type A bound nucleic acid probes.
Figure 2:
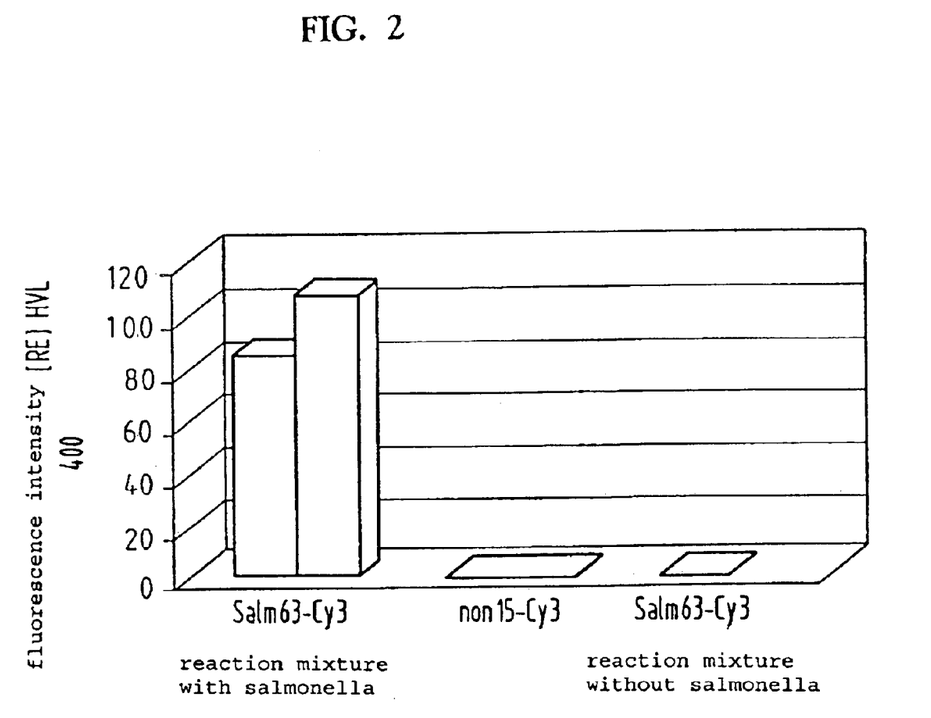
FIG. 2 shows the result of hybridization of ten cells of *S. typhimurium* LT2 inoculated in H milk after 13 hours of incubation at 37° C., 40% in HP, HVL 400.

Batch with *Salmonella*:

| Salm63-Cy3 | detects *Salmonella* species, supplies a specific signal |
| non15-Cy3 | nonsense probe representing nonspecific binding and background |

(control 1)

Batch without *Salmonella*:

Salm63-Cy3 detects *Salmonella* species, and it represents the background with the *Salmonella*-specific probe because no *Salmonella* were present in this batch (control 2).

EXAMPLE 1

Detection of bacteria of the genus *Salmonella* in milk

1. General Description:

The method described below, which is referred to as the "SalmoQuick method" according to this invention, is used for qualitative analysis of bacteria of the genus *Salmonella* in foods on the basis of the method according to this invention. *Salmonella* can be identified in 24 hours, so this yields a considerable speed advantage in comparison with conventional methods which take between 5 and 14 days for an identification, depending on the taxonomic accuracy.

2. Basic Principle:

*Salmonella* in milk is detected specifically by fluorescence-labeled oligonucleotide probes directed against rRNA. After suitably stringent washing steps, bound probes are released from their target cells in the bacteria and then are quantified in a fluorometer. A conclusion regarding whether or not *Salmonella* is present in milk can obtained on the basis of the height of the resulting fluorometer signal.

3. Brief Description:

The milk sample which is to be tested for the presence of *Salmonella* is incubated for several hours. This ensures that first, there are enough target sites for detection with probes due to the reproduction of any *Salmonella* that might be present in the milk, and secondly, only living *Salmonella* are identified. A shift in population due to incubation for several hours is not harmful, because not all bacteria need be identified and instead only the presence or absence of *Salmonella* is determined. After centrifugation and fixation of the cells, during which the cells are made accessible for the probes, the proteins which interfere with the subsequent hybridization can be removed sufficiently well by a lysis step. During the subsequent hybridization, the fluorescence-labeled oligonucleotide probes bind specifically to the rRNA or the bacteria of the genus *Salmonella* under sufficiently stringent conditions. The subsequent washing step ensures removal of the unbound probes. During another treatment procedure, the specifically bound probes are extracted from the cells. The fluorescence colors of these probes can then be quantified in a fluorometer. The height of the resulting signal provides information regarding whether or not *Salmonella* is present in the milk sample.

4. Technical Equipment:

4.1 Preparation of the Sample

The following equipment is needed to prepare a sample:

Sample container (Greiner, Nürtingen)

Circular shaker

Greiner centrifuge (8000 rpm)

Desk-top centrifuge (14,000 rpm)

4.2 In Situ Hybridization

The following are needed for in situ hybridization:

Desk-top centrifuge (14,000 rpm)

Heating block and water bath or two heating blocks

Hybridization oven 4.3 Quantification Equipment
Fluorometer, chemiluminometer or scintillator
5. Materials
5.1 Preparation of the Sample
The following material were used to process the sample, including cell fixation:

| | |
|---|---|
| 9 mL saline tube | 0.9% NaCl in distilled $H_2O$ |
| Tryptic soy medium (TS medium) | |
| casein peptone | 15.0 g |
| soy peptone | 5.0 g |
| NaCl | 5.0 g |
| $H_2O$ distilled to a total of 1 L pH 7.3 | |
| Lysis buffer | |
| $Na_2HPO_4$ | 100 mM |
| NaCl | 150 mM |
| EDTA | 10 mM |
| NaOH | 40 mM |
| PBS stock solution ($Na_xPO_4$) | |
| 200 mM $NaH_2PO_4$) | |
| 200 mM $Na_2HPO_4$ | pH 7.2–7.4 |
| 3 × PBS solution | |
| 390 mM NaCl | |
| 30 mM $Na_xPO_4$ (PBS stock solution) | pH 7.2–7.4 |
| 1 × PBS solution | |
| 130 mM NaCl | |
| 10 mM $Na_xPO_4$ (PBS stock solution) | pH 7.2–7.4 |
| 4% paraformaldehyde solution (PFA): | |

Can be prepared by adding 3 g paraformaldehyde to 30 mL double-distilled $H_2O$ heated to 60° C., adding 1 M NaOH by drops until the paraformaldehyde is dissolved completely, then adding 16.6 mL 3×PBS, cooling the solution to approximately 20° C., adjusting the pH with 1 M HCl to 7.2–7.4; sterile filtration of the finished PFA solution through a 0.2 μm filter (Millipore, Eschborn). The solution can be stored for approximately 1 week at 4° C.; freezing for several months is also possible.

5.2 In situ hybridization
Formamide (Merck, Darmstadt)
Probe working solution of 50 ng/μL each (specific and nonspecific probe)

| | |
|---|---|
| Separation buffer (2 mL): | |
| 0.01 M Tris/HCl, pH 9.0 | |
| Hybridization buffer (HP, 2 mL with x% formamide content): | |
| 5 M NaCl | 360 μL |
| 1 M Tris/HCl pH 8.0 | 40 μL |
| Formamide | y μL |
| 10% (w/v) SDS | 2 μL |
| $H_2O$ double-distilled to a total of 2 mL | |
| Washing buffer (2 mL): | |
| 5 M NaCl | 18.4 μL |
| 1 M Tris/HCl pH 8.0 | 40 μL |
| 0.5 M EDTA pH 8.0 | 20 μL |
| 10% (w/v) SDS | 2 μL |
| $H_2O$, double-distilled, to a total of 2 mL | |

Probes:
Salm63: 5'-TCGACTGACTTCAGCTCC-3' (SEQ ID NO:1)
NonSalm: 5'-GCTAACTACTTCTGGAGC-3' (SEQ ID NO:2)
Fluorescence dye used: Cy3

6. Procedure
6.1 Preparation of milk
1. Preheat milk samples and TS medium at 37° C. for approximately 20 minutes.
2. Add 25 mL preheated TS medium to 25 mL preheated milk in a sample container with a capacity of 50 mL.
3. Incubate overnight at 30° C. (13 hours) on a circular shaker.
4. Centrifuge the 50 mL sample containers at 8000 rpm for 8 minutes to harvest the cells.
5. Resuspend the pellets with 25 mL lysis buffer to separate proteins and fats of milk from the cells and then incubate for 10 minutes at RT (room temperature).
6. Centrifuge for 8 minutes at 8000 rpm.
7. Repeat the steps of resuspending and incubating with lysis buffer (see 5).
8. Centrifuge for 8 minutes at 8000 rpm.
9. Resuspend the pelletized cells in 600 μL 1×PBS and transfer to an Eppendorf reaction vessel. Rinse in 50 mL sample vessel with 600 μL 1×PBS.
10. Centrifuge the Eppendorf reaction vessels at 14,000 rpm for 6 minutes.
11. Discard the supernatant and resuspend the cells in 1 mL 1×PBS.
12. Centrifuge the Eppendorf reaction vessels at 14,000 rpm for 6 minutes.
13. Discard the supernatant and completely resuspend the pellet in 200 μL 1×PBS.
14. Add 600 μL of a freshly prepared 4% paraformaldehyde solution.
15. Incubate for 1 hour at 4° C.
16. Centrifuge at 14,000 rpm for 6 minutes.
17. Discard the supernatant and completely resuspend the pellet in 1 mL 1×PBS.
18. Centrifuge at 14,000 rpm for 6 minutes.
19. Discard the supernatant (pellet remains in the cap).

6.2 In situ hybridization
1. Preheat the hybridization buffer to 48° C. in a water bath or in a heating block for approximately 20 minutes.
2. Transfer the Eppendorf reaction vessel (with the cell pellet remaining in it) to the heating block (preheated to 80° C.) and incubate for 5 minutes at 80° C.
3. After incubating for 5 minutes at 80° C., add 80 μL of the preheated hybridization buffer to each Eppendorf reaction vessel.
4. Add 2.5 μL of the freshly thawed Salm63-Cy3 probe working solution to two each of four milk sample batches.
5. Add 2.5 μL of the freshly thawed nonSalm63-Cy3 probe working solution to each of the two remaining milk sample batches.
6. Mix the Eppendorf reaction vessel vigorously for 10 seconds and centrifuge briefly (2 seconds) by means of a small desk-top centrifuge.
7. Incubate the Eppendorf reaction vessels for 2 hours at 46° C. in the hybridization oven, in a water bath or in a heating block (hybridization of the probe with the target sequence under stringent conditions).
8. Preheat the washing buffer at 48° C. in a water bath or in a heating block.
9. After incubating for 2 hours at 46° C., centrifuge the Eppendorf reaction vessels at 14,000 rpm for 6 minutes.
10. Completely remove and discard the supernatant using a 200 μL pipette without touching the pellet.
11. Add 100 μL preheated washing buffer, mix the Eppendorf reaction vessels vigorously for 5 seconds and transfer to a water bath at 48° C. for 20 minutes (removing the unbound probe molecules under stringent conditions).

12. Preheat the separation buffer at 80° C. in a heating block.
13. After incubating for 20 minutes at 48° C., centrifuge the Eppendorf reaction vessels at 14,000 rpm for 6 minutes.
14. Completely remove the supernatant by using a 200 µL pipette and discard without touching the pellet.
15. Add 110 µL preheated separation buffer, mix thoroughly in the Eppendorf reaction vessels for 5 seconds and then transfer to the heating block at 80° C. for 15 minutes (separating the probe from the target sequence).
16. After incubating for 15 minutes at 80° C., centrifuge the Eppendorf reaction vessels at 14,000 rpm for 6 minutes.
17. Cautiously transfer the supernatant to new 1.5 mL reaction vessels by using a 200 µL pipette without touching the pellet and then store on ice in the dark until performing the measurement.
18. Turn on the fluorometer and set the wavelength at 550 nm for excitation (excitation wavelength) and 570 nm (emission wavelength) to measure the emission of the Cy3 dye.
19. Set the high voltage level at the desired sensitivity (400 to 800 HVL).
20. Add 107 µL separation buffer to a precision glass cuvette for performing fluorometry.
21. Set the fluorometer at zero (autozero).
22. Preheat the Eppendorf reaction vessels to room temperature briefly by warming in the hand for 5 seconds before performing the measurements.
23. Add the separation buffer containing the separated probe to the precision glass cuvette for fluorometry and measure the signal.
24. Read the signal after 10 seconds, because after opening the cover of the light channel, the signal is stable after 5 to 8 seconds.
25. The fluorescence value of the milk sample tested= fluorescence value of the milk sample hybridized with Salm63-Cy3 minus the fluorescence value of the milk sample hybridized with nonSalm-Cy3.
7. Result The result of the experiment described above is illustrated in FIG. 2, where it can be seen clearly that the *Salmonella*-specific signal is many times higher than a nonspecific binding which was also tested. The probe background was hardly detectable.

EXAMPLE 2

Detection of bacteria of the genus *Salmonella* in 25 mL milk or 25 g milk powder Batch of two milk samples of 25 mL each or 25 g for hybridization with the probes
"Salm63-Cys" (Cy3-5'-TCGACTGACTTCAGCTCC-3' (SEQ ID NO:1)) and
"nonSalm-Cy3" (Cy3-5'-GCTAACTACTTCTGGAGC-3' (SEQ ID NO:2))
A. Cell fixation:
Laboratory equipment:
100 mL and 1 L Erlenmeyer flasks
Circular shaker
Sample container (Greiner, Nürtingen)
Greiner centrifuge (8000 rpm)
Desk-top centrifuge (14,000 rpm)
Materials:
9 mL saline tubes, 0.9% NaCl in distilled $H_2O$
Buffered peptone water (according to § 35 LMBG [(German) Food and Utilitarian Articles Act] with added malachite green

| | |
|---|---|
| Meat peptone | 10.0 g |
| NaCl | 5.0 g |
| Dibasic sodium phosphate (12 $H_2O$) | 9.0 g |
| Monobasic potassium phosphate | 1.5 g |
| Malachite green (oxalate) | 0.1 g |
| $H_2O$ distilled to a total of 1 L, pH 7.2 +/− 0.2 | |

Pour 225 mL portions into 1 L Erlenmeyer flask and 30 mL portions into 100 mL Erlenmeyer flask and autoclave for 15 minutes at 121° C.
Lysis Buffer:

| Lysis buffer: | |
|---|---|
| $Na_2HPO_4$ | 100 mM |
| NaCl | 150 mM |
| EDTA | 10 mM |
| NaOH | 40 mM |

Solutions used for PFA cell fixation:

| PBS stock solution ($Na_xPO_4$) |
|---|
| 200 mM $NaH_2PO_4$ |
| 200 mM $Na_2HPO_4$ pH 7.2–7.4 |
| 3 × PBS solution |
| 390 mM NaCl |
| 30 mM $Na_xPO_4$ (PBS stock solution) pH 7.2–7.4 |
| 1 × PBS solution |
| 130 mM NaCl |
| 10 mM $Na_xPO_4$ (PBS stock solution) pH 7.2–7.4 |
| 4% paraformaldehyde (PFA): |

4% paraformaldehyde (PFA):
This solution can be prepared by adding 3 g paraformaldehyde to 30 mL double-distilled $H_2O$ heated to 60° C., then adding 1 M NaOH by drops until the paraformaldehyde has dissolved completely, next adding 16.6 mL 3×PBS, cooling the solution to approximately 20° C., adjusting the pH with 1 M HCl to 7.2–7.4, and sterile filtration of the finished PFA solution through a 0.2 µm filter (Millipore, Eschborn). The solution can be stored for approximately one week at 4° C. It can also be stored frozen for several months.
Procedure:
1. Preheat 225 mL buffered peptone water with added malachite green at 37° C. for approximately 1 hour.
2. Add 25 mL milk or 25 g milk powder to 225 mL preheated buffered peptone water containing added malachite green and mix thoroughly.
3. Incubate for 7.5 hours at 37° C. on the circular shaker.
4. Remove 1 mL from the incubated batch under sterile conditions and transfer to 30 mL buffered peptone water with added malachite green.
5. Incubate overnight (at least 14 hours) at 37° C. on a circular shaker.
6. Transfer the incubated 30 mL batches to 50 mL sample vessels for harvesting the cells.
7. Centrifuge the sample vessels at 8000 rpm for 8 minutes.
8. Resuspend the pellets with 20 mL lysis buffer to separate the proteins and fats of the milk from the cells and then incubate for 10 minutes at RT.
9. Centrifuge for 8 minutes at 8000 rpm.
10. Resuspend the pelletized cells in 600 µL 1×PBS and transfer to a 2 mL reaction vessel. Rinse the 50 mL sample vessel with 600 µL 1×PBS.

11. Centrifuge the reaction vessels at 14,000 rpm for 6 minutes.
12. Discard the supernatant and resuspend the cells in 1 mL 1×PBS.
13. Centrifuge the Eppendorf reaction vessels at 14,000 rpm for 6 minutes.
14. Discard the supernatant and completely resuspend the pellets in 450 µL 1×PBS.
15. Add 1350 µL of a freshly thawed paraformaldehyde solution.
16. Incubate for 1 hour at 4° C.
17. Transfer 800 µL into each of two 1.5 mL Eppendorf reaction vessels for subsequent hybridization with Salm63-Cy3 and nonSalm-Cy3.
18. Centrifuge at 14,000 rpm for 6 minutes.
19. Remove and discard the supernatant and completely resuspend the pellet in 1 mL 1×PBS.
20. Centrifuge at 14,000 rpm for 6 minutes.
21. Remove and discard the supernatant (the pellet remains in the cap).

B. Hybridization

Laboratory equipment:
Desk-top centrifuge (14,000 rpm)
Fluorometer (Kontron Instruments SFM 25)
Heating block and water bath or two heating blocks (48° C. and 80 C)
Hybridization oven (46 C)
Materials
Formamide (Merck, Darmstadt)
Probe working solutions of 50 ng/µL each: 25 µL Salm63-Cy3, 25 µL nonSalm-Cy3

| Separation buffer (2 mL): | |
|---|---|
| 0.01 M Tris/HCl | ph 9.0 |
| Hybridization buffer (2 mL with 40% formamide content): | |
| 5 M NaCl | 360 µL |
| 1 M Tris/HCl, pH 8.0 | 40 µL |
| Formamide | 800 µL |
| 10% (w/v) SDS | 2 µL |
| H$_2$O double-distilled to a total of 2 mL | |
| Washing buffer (2 mL): | |
| 5 M NaCl | 18.4 µL |
| 1 M Tris/HCl, pH 8.0 | 40 µL |
| 0.5 M EDTA, pH 8.0 | 20 µL |
| 10% (w/v) SDS | 2 µL |
| H$_2$O double-distilled to a total of 2 mL | |

Procedure:
1. Preheat the hybridization buffer to 48° C. for approximately 20 minutes in a water bath or a heating block.
2. Transfer the Eppendorf reaction vessels (with the remaining cell pellet) to the heating block (preheating to 80° C.) and incubate for 5 minutes at 80° C.
3. After incubation at 80° C. for 5 minutes, add 160 µL of the preheated hybridization buffer to each Eppendorf reaction vessel.
4. Add 3.0 µL of the freshly thawed Salm63-Cy3 probe working solution to each of the two parallel batches.
5. Add 3.0 µL of the freshly thawed nonSalm-Cy3 probe working solution to each of the two remaining parallel batches.
6. Whirl (vortex) the Eppendorf reaction vessels for 10 seconds and centrifuge briefly (2 seconds) in a small desk-top centrifuge.
7. Incubate the Eppendorf reaction vessels for 2 hours at 46° C. in a hybridization oven or in a water bath or a heating block (hybridization of the probe with the target sequence under stringent conditions).
8. Preheat the washing buffer to 48° C. in a water bath or in a heating block.
9. After incubation for 2 hours at 46° C., centrifuge the Eppendorf reaction vessels at 14,000 rpm for 6 minutes.
10. Completely remove and discard the supernatant using a 200 µL pipette without touching the pellet.
11. Add 180 µL preheated washing buffer, whirl the Eppendorf reaction vessels for 5 seconds and transfer to a water bath at 48° C. for 20 minutes (removing the unbound probe molecules under stringent conditions).
12. Preheat approximately 1.4 mL separation buffer to 80° C. in a heating block.
13. After incubating at 48° C. for 20 minutes, centrifuge the Eppendorf reaction vessels at 14,000 rpm for 6 minutes.
14. Completely remove and discard the supernatant using a 200 RL pipette without touching the pellet.
15. Add 130 µL preheated separation buffer, whirl the Eppendorf reaction vessel for 5 seconds and transfer to the heating block at 80° C. for 15 minutes (separation of the probe from the target sequence).
16. After incubation at 80° C. for 15 minutes, centrifuge the Eppendorf reaction vessels at 14,000 rpm for 6 minutes.
17. Cautiously transfer the supernatant using a 200 µL pipette to new 1.5 mL reaction vessels without touching the pellet and then store on ice in the dark until the measurement is performed.
18. Turn on the fluorometer and set the wavelengths at 550 nm for excitation (excitation wavelength) and at 570 nm (emission wavelength) to measure the emission of the Cy3 dye.
19. Set the high voltage level at the desired sensitivity (400 to 800 HVL).
20. Add 108 µL separation buffer to a precision glass cuvette for fluorometry.
21. Set the fluorometer at zero (auto zero).
22. Preheat the Eppendorf reaction vessels briefly to room temperature by holding in your hand for 5 seconds before performing the measurement.
23. Add the separation buffer containing the separated probe to the precision glass cuvette for fluorometry and measurement of the signal.
24. Read the signal after 10 seconds because the signal is stable after 5 to 8 seconds after opening the cover of the light channel.
25. Fluorescence value of the milk sample tested fluorescence value of the milk sample hybridized with Salm63-Cy3 minus the fluorescence value of the milk sample hybridized with nonSalm-Cy3.

EXAMPLE 3

Use of the fast FISH technique for relative quantification of bacterial populations in activated sludge (on the example of PPx3)

A. Cell fixation:
Laboratory equipment:
2 mL reaction vessels
Desk-top centrifuge (14,000 rpm)
Solutions used for PFA cell fixation:

| PBS stock solution (Na$_x$PO$_4$) | |
|---|---|
| 200 mM NaH$_2$PO$_4$ | |
| 200 mM Na$_2$HPO$_4$ | pH 7.2–7.4 |

-continued

3 × PBS solution 390 mM NaCl
30 mM Na$_x$PO$_4$ (PBS stock solution)  pH 7.2–7.4
1 × PBS solution 130 mM NaCl
10 mM Na$_x$PO$_4$ (PBS stock solution)  pH 7.2–7.4
4% paraformaldehyde (PFA):

4% paraformaldehyde (PFA):

This solution can be prepared by adding 3 g paraformaldehyde to 30 mL double-distilled H$_2$O heated to 60° C., adding 1 M NaOH by drops until the paraformaldehyde has dissolved completely, then adding 16.6 mL 3×PBS, cooling the solution to approximately 20° C., adjusting the pH with 1 M HCl to 7.2–7.4, sterile filtration of the finished PFA solution through a 0.2 μm filter (Millipore, Eschborn). The solution can be stored for approximately one week at 4° C. It can also be stored frozen for several months.

Procedure:
1. Add three parts 4% paraformaldehyde solution to one part freshly drawn activated sludge sample (e.g., 30 mL 4% paraformaldehyde solution to 10 mL activated sludge).
2. Incubate for 3 hours at 4° C.
3. Centrifuge for 6 minutes at 8000 rpm.
4. Discard the supernatant and completely resuspend the pellet in 1 mL 1×PBS.
5. Centrifuge for 6 minutes at 8000 rpm.
6. Discard the supernatant (pellet remains in the cap).
7. Resuspend the pellet in 250 μL 1×PBS.
8. Add 250 μL ethanol at −18° C.
9. Whirl thoroughly and optionally store at −18° C. (fixed activated sludge sample).

B. Hybridization

Laboratory equipment:

Desk-top centrifuge (14,000 rpm)
Fluorometer
One heating block and one water bath or two heating blocks
Hybridization oven Materials:

Eppendorf 1.5 mL reaction vessels
Formamide (Merck, Darmstadt)
Probe working solutions of 50 ng/μL each:

25 μL PPx3 655-Cy3: 5'-ACC CTC CTC TCC CGG TCT-3' (SEQ ID NO:3)

As an alternative to PPx3 655-Cy3, it is also possible to use PPx3 1428-Cy3

```
PPx3 1428-Cy3      5'-TGG CCC ACC GGC TTC GGG-3'

25 μL Non15-Cy3    5'-GCT AAC TAC TTC TGG AGC-3'

25 μL Non15-Cy5    5'-GCT AAC TAC TTC TGG AGC-3'

25 μL 3xEUB-       5'-GCT GCC TCC CGT AGG AGT-3'
Cy3I.              II.  5'-GCA GCC ACC CGT AGG TGT-3'
                   III. 5'-GCT GCC ACC CGT AGG TGT-3'

25 μL 3xEUB-       5'-GCT GCC TCC CGT AGG AGT-3'
Cy5I.              II.  5'-GCA GCC ACC CGT AGG TGT-3'
                   III. 5'-GCT GCC ACC CGT AGG TGT-3'
```

Separation buffer (2 mL):
0.01 M Tris/HCl, pH 9.0

Hybridization buffer (2 mL with 20% formamide content):

| | |
|---|---|
| 5 M NaCl | 360 μL |
| 1 M Tris/HCl, pH 8.0 | 40 μL |
| Formamide | 400 μL |
| 10% (w/v) SDS | 2 μL |
| H$_2$O double-distilled to a total of 2 mL | |

Washing buffer (2 mL):

| | |
|---|---|
| 5 M NaCl | 86 μL |
| 1 M Tris/HCl, pH 8.0 | 40 μL |
| 0.5 M EDTA, pH 8.0 | 20 μL |
| 10% (w/v) SDS | 2 μL |
| H$_2$O, double-distilled, to a total of 2 mL | |

Batch (for exact procedure, see "Procedure"):
1. 2×defined volumes of fixed activated sludge sample (10 to 100 μL)+3×Eub-Cy3
2. 2×defined volumes of fixed activated sludge sample+ 3×Eub-Cy5
3. 2×defined volumes of fixed activated sludge sample+ Non15-Cy3
4. 2×defined volumes of fixed activated sludge sample+ Non15-Cy5
5. 2×defined volumes of fixed activated sludge sample+ 3×Eub-Cy5+PPX3 655-Cy3

Procedure:
1. Preheat the hybridization buffer to 48° C. in a water bath or in a heating block for approximately 20 minutes.
2. Transfer a defined volume of PFA-fixed activated sludge sample (10 to 100 μL) to Eppendorf reaction vessels.
3. Centrifuge for 6 minutes at 14,000 rpm.
4. Remove the supernatant using a 200 μL pipette and discard without touching the pellet.
5. Transfer the Eppendorf reaction vessels (with the remaining cell pellet) to a heating block (preheated to 80° C.) and incubate for 5 minutes at 80° C.
6. After incubating for 5 minutes at 80° C., add 80 μL of the preheated hybridization buffer to each Eppendorf reaction vessel.
7. Add 2.5 μL of the corresponding freshly thawed probe working solution to each of the activated sludge batches (see under "Batch").
8. Whirl the Eppendorf reaction vessels for 10 seconds and centrifuge briefly (2 seconds) by using a small desk-top centrifuge.
9. Incubate the Eppendorf reaction vessels for 2 hours at 46° C. in a hybridization oven or in a water bath or a heating block (hybridization of the probe with the target sequence under stringent conditions).
10. Preheat the washing buffer to 48° C. in a water bath or in a heating block.
11. After incubating for 2 hours at 46° C., centrifuge the Eppendorf reaction vessels at 14,000 rpm for 6 minutes.
12. Completely remove all the supernatant using a 200 μL pipette and discard without touching the pellet.
13. Add 100 μL preheated washing buffer, whirl the Eppendorf reaction vessels for 5 seconds and transfer to a water bath at 48° C. for 20 minutes (removing the unbound probe molecules under stringent conditions).
14. Preheat the separation buffer to 80° C. in a heating block.
15. After incubating at 48° C. for 20 minutes, centrifuge the Eppendorf reaction vessels for 6 minutes at 14,000 rpm.
16. Completely remove the supernatant using a 200 μL pipette and discard without touching the pellet.

17. Add 110 μL preheated separation buffer, whirl the Eppendorf reaction vessel for 5 seconds and transfer it to the heating block at 80 CC for 15 minutes (separating the probe from the target sequence).
18. After incubating at 80° C. for 15 minutes, centrifuge the Eppendorf reaction vessels for 6 minutes at 14,000 rpm.
19. Cautiously transfer the supernatant using a 200 μL pipette to new 1.5 mL reaction vessels without touching the pellet and then store on ice in the dark until performing the measurement.
20. Turn on the fluorometer.
21. In order to measure the Cy3 marked probes, set the wavelengths at 550 nm for excitation (excitation wavelength) and at 570 nm (emission wavelength) to measure the emission.
22. For measuring the Cy5 marked probes, set the wavelength for excitation at 644 nm (excitation wavelength) and to measure the emission, set the wavelength at 659 nm (emission wavelength).
23. In the case of batches with both dyes (PPx3-Cy3 and 3xEub-Cy5), always determine the Cy5 value first and then determine the Cy3 value (because of bleaching effects).
24. Set the high voltage level at the desired sensitivity (400 to 800 HVL).
25. Add 108 μL separation buffer to a precision glass cuvette for fluorometry.
26. Set the fluorometer at zero (autozero).
27. Preheat the Eppendorf reaction vessels briefly to room temperature by holding in the hand for 5 seconds before performing the measurement.
28. Add the separation buffer containing the separated probe to the precision glass cuvette for fluorometry and measure the signal.
29. Read the signal after 10 seconds because the signal is stable 5 to 8 seconds after opening the cover of the light channel.

Calculating the relative amount of PPx3 cells in the activated sludge tested:

Average measured value of the activated sludge sample (BP) with 3xEub-Cy

=Correction factor

Average measured value of BP with 3xEub-Cy5

Relative amount of PPx3 cells in percentage=

(Measured value BP with PPx3-Cy3−Average measured value BP with Non15-Cy3)×100

(Measured value BP with 3xEub-Cy5−Average measured value BP with Non15-Cy5)×Correction factor

---

What is claimed is:

1. A method of detecting microorganisms in a sample
   a) fixing the microorganisms contained in the sample;
   b) incubating the fixed microorganisms with detectable nucleic acid probe molecules which are capable of hybridizing to a target nucleic acid of the microorganism to be detected so as to form a complex between the detectable nucleic acid probe molecules and the target nucleic acid;
   c) removing nonhybridized nucleic acid probe molecules from the fixed microorganisms;
   d) incubating the fixed microorganisms with a separation solution at a temperature at or above 80° C. and up to 100° C. which denatures the detectable nucleic acid probe molecules from the target nucleic acid, yielding separated nucleic acid probe molecules wherein the separation solution is selected from the group consisting of water, DMSO, 1×SSC and 0.001–0.01 M Tris/HCl, pH 9.0+/−2.0; and
   e) detecting the separated nucleic acid probe molecules, wherein the presence of the separated nucleic acid probe molecules correlates with the presence of the microorganism in the sample, and wherein the detection signal associated with the separated nucleic acid probe molecules is greater than that with separated nucleic acid probe molecules obtained by incubation in a formamide separation solution.

2. A method according to claim 1, wherein the separated nucleic acid probe molecules in step e) are also quantified.

3. A method according to claim 1, wherein the nucleic acid probe molecules are complementary to a chromosomal or episomal DNA, an mRNA or rRNA of a microorganism to be detected.

4. A method according to claim 1, wherein the detectable nucleic acid probe molecules comprise nucleic acid probe molecules covalently bonded to a detectable marker.

5. A method according to claim 4, wherein the detectable marker is selected from the group of the following markers:
   a) fluorescence markers,
   b) chemoluminescence markers,
   c) radioactive markers, d) enzymatically active group, e) haptene, f) nucleic acid detectable by hybridization.

6. A method according to claim 1, wherein the microorganism is a single-cell microorganism.

7. A method according to claim 1, wherein the microorganism is a yeast, a bacterium, an alga or a fungus.

8. A method according to claim 7, wherein the microorganism belongs to the genus *Salmonella*.

9. A method according to claim 1, wherein the sample is an environmental sample taken from water, soil or air.

10. A method according to claim 1, wherein the sample is a food sample.

11. A method according to claim 10, wherein the sample is taken from milk or milk products, drinking water, beverage, baked products or meat products.

12. A method according to claim 1, wherein the sample is a medicinal sample.

13. A method according to claim 12, wherein the sample is taken from tissue, secretions or fecal matter.

14. A method according to claim 1, wherein the sample is taken from wastewater.

15. A method according to claim 14, wherein the sample is taken from activated sludge, putrefactive sludge or anaerobic sludge.

16. A method according to claim 1, wherein the sample is taken from a biofilm.

17. A method according to claim 16, wherein the biofilm is taken from an industrial plant, is formed in purification of wastewater or is a naturally occurring biofilm.

18. A method according to claim 1, wherein the sample is taken from a pharmaceutical or cosmetic product.

19. A method of detecting microorganisms in a sample a) incubating a sample comprising fixed microorganisms with detectable nucleic acid probe molecules which are capable of hybridizing to a target nucleic acid of the microorganism to be detected so as to form a complex between the detectable nucleic acid probe molecules and the target nucleic acid of the microorganism;

b) removing nonhybridized nucleic acid probe molecules from the fixed microorganisms;

c) incubating the fixed microorganisms with a separation solution at a temperature at or above 80° C. and up to 100° C. which denatures the nucleic acid probe molecules from the target nucleic acid, yielding separated nucleic acid probe molecules, wherein the separation solution is selected from the group consisting of water, DMSO, 1×SSC and 0.001–0.01 M Tris/HCl, pH 9.0+/−2.0; and d) detecting the separated nucleic acid probe molecules, wherein the presence of the separated nucleic acid probe molecules correlates with the presence of the microorganism in the sample, and wherein the detection signal associated with the separated nucleic acid probe molecules is greater than that with separated nucleic acid probe molecules obtained by incubation in a formamide separation solution.

20. The method of claim 1 or 19 further comprising isolating the separated nucleic acid molecules prior to detection.

21. The method of claim 20 wherein the separated nucleic acid molecules are isolated by centrifugation.

* * * * *

UNITED STATES PATENT AND TRADEMARK OFFICE
CERTIFICATE OF CORRECTION

PATENT NO. : 6,844,157 B2
DATED : January 18, 2005
INVENTOR(S) : Snaidr

It is certified that error appears in the above-identified patent and that said Letters Patent is hereby corrected as shown below:

Title page,
Item [56], References Cited, U.S. PATENT DOCUMENTS, delete "Sanders" and insert -- Sanders et al.. --, therefor.

Column 21,
Line 48, after "sample" insert -- comprising: --.
Line 62, after "molecules" insert -- , --.

Column 24,
Line 1, after "sample" insert -- comprising: --.

Signed and Sealed this

Twenty-fourth Day of May, 2005

JON W. DUDAS
*Director of the United States Patent and Trademark Office*

SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
tcgactgact tcagctcc                                                 18

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
gctaactact tctggagc                                                 18

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
accctcctct cccggtct                                                 18

<210> SEQ ID NO 4
<211> LENGTH: 18
<212> TYPE: DNA
<213> ORGANISM: Artificial Sequence
<220> FEATURE:
<223> OTHER INFORMATION: Primer -continued

```
<400> SEQUENCE: 4
tggcccaccg gcttcggg                                                        18

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gctaactact tctggagc                                                        18

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
gctgcctccc gtaggagt                                                        18

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gcagccaccc gtaggtgt                                                        18

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
gctgccaccc gtaggtgt                                                        18
```